United States Patent [19]

DeVaughn et al.

[11] Patent Number: 5,580,529
[45] Date of Patent: Dec. 3, 1996

[54] AEROSOL AND LIQUID TRANSFER RESISTANT PIPETTE TIP APPARATUS

[75] Inventors: Donald H. DeVaughn, San Francisco; James C. Smith, Hayward, both of Calif.

[73] Assignee: Bio-Plas, Inc., San Francisco, Calif.

[21] Appl. No.: 489,506

[22] Filed: Jun. 12, 1995

Related U.S. Application Data

[63] Continuation of Ser. No. 231,405, Apr. 22, 1994, abandoned.

[51] Int. Cl.⁶ ..................... B01L 3/02
[52] U.S. Cl. ............. 422/101; 422/100; 422/103; 436/178; 436/180; 73/864.03; 73/864.14; 210/477
[58] Field of Search ............... 422/99, 100, 101, 422/103; 436/177, 180; 73/864.03, 864.11, 864.14; 210/473, 477

[56] References Cited

U.S. PATENT DOCUMENTS

| | | | |
|---|---|---|---|
| 2,348,831 | 5/1944 | Mathis | 422/100 |
| 2,396,470 | 3/1946 | Mortensen | 422/100 |
| 2,423,173 | 7/1947 | Brady et al. | 422/100 |
| 2,692,503 | 10/1954 | Crecelius | 422/100 |
| 3,864,979 | 2/1975 | Ayers | 422/100 |
| 3,995,496 | 12/1976 | Bickford | 73/425.6 |
| 4,059,020 | 11/1977 | Avakian | 73/425.4 |
| 4,933,148 | 6/1990 | Perlman | 422/100 |
| 4,999,164 | 3/1991 | Puchinger et al. | 422/100 |
| 5,156,811 | 10/1992 | White | 422/100 |

*Primary Examiner*—Long V. Le
*Attorney, Agent, or Firm*—Flehr, Hohbach, Test, Albritton & Herbert

[57] ABSTRACT

A baffle assembly (23) positioned between a pipetter assembly (10) and a disposable pipette tip (16) for substantially reducing transfer of aerosol and/or fluid specimens to the pipetter. The baffle assembly (23) includes a barrier structure (25) extending transversely across a receiving chamber (17) of the pipette tip (16) and defines at least one narrow passageway (26) extending generally in the direction of the longitudinal axis (27) through the barrier member (25) between an entrance (30) and an exit (31) thereof. The passageway (26) includes a first wall (32) extending generally transverse, and preferably perpendicular to, the longitudinal axis (27) of the pipette tip to define at least one elbow portion positioned between the entrance (30) and the exit (31) of the passageway. A filter membrane (55) preferably is secured across the passageway (26) to reduce aerosol transport through the passageway (26). A method for substantially reducing transfer of aerosol and/or fluid to the pipetter (10) is also provided, as is a method for securing the filter (55) to the baffle assembly (23).

16 Claims, 2 Drawing Sheets

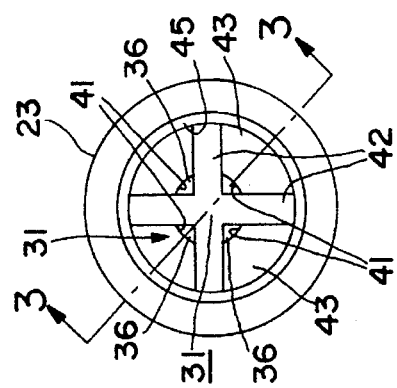
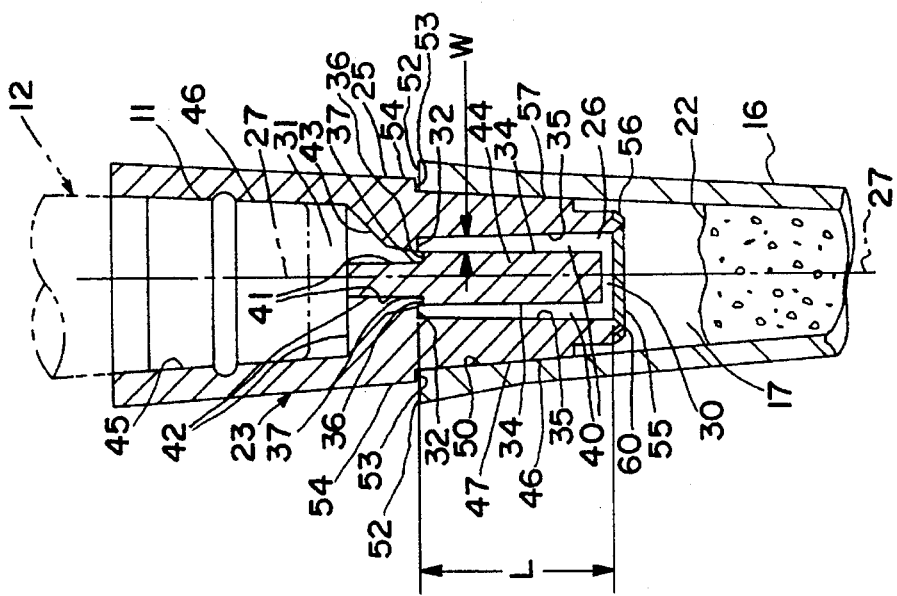
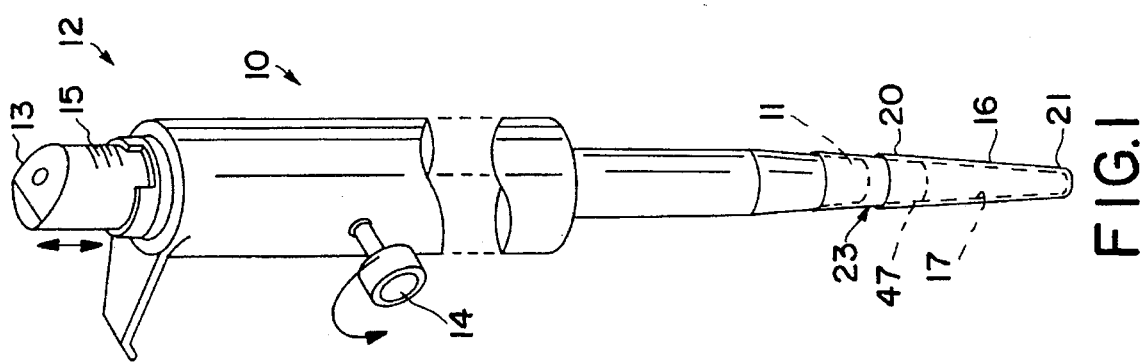

AEROSOL AND LIQUID TRANSFER RESISTANT PIPETTE TIP APPARATUS

This is a continuation of application Ser. No. 08/231,405 filed Apr. 22, 1994, now abandoned.

TECHNICAL FIELD

The present invention relates, in general, to pipette tips, and more particularly, relates to aerosol and liquid transfer resistant pipette tips.

BACKGROUND ART

In recent years, the use of plastic, disposable pipette tips has expanded rapidly. In biotechnology and medical research, such as polymerase chain reactions (PCR), tissue culture, serological assays, forensic assays, nucleic acid or protein loadings and pipetting of radioactive samples, there are now literally hundreds of millions of these tips used in the United States each year. Typically, the plastic tips are used with pipetters, and in most applications each tip is used once and then disposed of so as to avoid contamination and eliminate the need for cleaning of the tips. Thus, a single pipetter will be used with hundreds and even thousands of disposable tips in the course of a week.

Although disposal of these tips has substantially reduced cross-contamination of samples, this problem still occurs, most commonly caused by carry over from one test tube to another. Another cause of contamination, however, is due to exposure of the pipetter barrel and shaft of conventional air-displacement micropipetters with aerosols generated during aspiration of fluid samples into and out of the disposable pipette tips. In certain situations, such as in PCR, which provides a method to produce multiple copies of a specific nucleotide sequence from small quantities of DNA, the reactions are so sensitive that even a minute exposure may be critical. Hours or even days of laboratory research may be wasted due to this contamination.

Yet another form of contamination of the pipetter barrel may be caused by fluid absorption from substances such as amplified DNA, radioisotopes, or infectious materials due to actual contact of the sample therewith. Contact with the fluid is often caused by uncalibrated pipetters or shoddy technique, such as overdraw and tipping of the pipetter, or mishandling which causes splashing during the drawing phase of pipetting.

To overcome these problems, positive displacement pipetters have been employed to reduce cross-contamination of samples caused by aerosol contamination of the pipetter barrel. These pipetters, however, are limited in use due to their cost, complexity, and time consumption during applications, especially when multiple pipetting is necessary.

Another attempt to eliminate aerosol and fluid sample contact contamination of the pipetter barrel involves wedging a relatively thick filter membrane into a receiving chamber defined by the dispensable pipette tip. The filter forms an aerosol and liquid interactive sealing barrier between the drawn fluid and the pipetter barrel. Typical of this invention is the device disclosed in U.S. Pat. No. 5,156,811.

While this arrangement has been effective to reduce aerosol contamination of the pipetter barrel, several problems are inherent with these designs. For instance, each filter must be individually positioned inside each pipetter tip which is an enormous and laborious undertaking, especially with the standard 8×12 array micro-titer plates (i.e., 96 tip racks) employed during manufacture. Further, since the filter membranes are frictionally secured by pushing them down into the receiving chamber, critical storage and dispensing capacity are reduced by the filter membrane. Hence, the full volumetric capabilities of the pipette tips having filters mounted therein are not realized. Upon contact of the filter with the sample fluid, these pipette tips require immediate replacement since a sealing gel barrier is formed in the filter which is liquid and gas impenetrable. Moreover, the relatively thick filter membrane adds resistance to fluid drawing and dispensing, which may reduce pipetting accuracy.

DISCLOSURE OF INVENTION

Accordingly, it is an object of the present invention to provide a pipetter assembly and method which reduces aerosol contamination of the pipetter.

Yet another object of the present invention to provide a pipetter assembly and method which reduces the chance of liquid transfer to the pipetter.

Another object of the present invention to provide a method of mounting a filter membrane to a pipetter baffle assembly.

It is a further object of the present invention to provide a pipetter assembly and method which is durable, compact, easy to maintain, has a minimum number of components, and is economical to manufacture.

In accordance with the foregoing objects, one embodiment of the present invention provides a pipetter apparatus including a pipetter assembly formed for drawing and dispensing a liquid, a pipette tip device, and a liquid/aerosol baffle assembly mounted between the tip and pipetter. The pipette tip has a liquid drawing end and an opposite pipetter securing end, and the securing end is formed for removable securement of the pipette tip to a tip mounting end of the pipetter. A liquid baffle assembly is positioned between the pipette tip and the pipetter and is formed to substantially reduce the transfer of liquid and liquid aerosols from the pipette tip to the pipetter.

The baffle assembly includes a barrier member extending transversely across a liquid receiving chamber of the baffle assembly, which barrier member defines at least one narrow circular passageway extending generally in the direction of the longitudinal axis of the baffle assembly. The passageway includes a first wall extending generally perpendicular to the longitudinal axis to define at least one elbow portion in the passageway in order to prevent direct aspiration or overdraw through the baffle assembly to the pipetter.

The pipetter apparatus may also include an aerosol resistant filter member heat sealed to a distal end of the barrier member in the baffle assembly in a manner substantially reducing transfer of aerosol from the liquid to the pipetter assembly.

In another aspect of the present invention, a method of mounting an aerosol resistant filter member to a heat deformable nose portion of a baffle assembly for a pipetter is provided comprising the steps of: positioning a filter member over the entrance in a barrier member of a baffle assembly; and heating a perimeter of the filter member while in abutting contact with the barrier member to a sufficient temperature to form a heat seal therebetween. The sealed filter substantially reduces transfer of aerosol through the baffle assembly to the pipetter assembly.

BRIEF DESCRIPTION OF THE DRAWING

The assembly of the present invention has other objects and features of advantage which will be more readily apparent from the following description of the Best Mode of Carrying Out the Invention and the appended claims, when taken in conjunction with the accompanying drawing, in which:

FIG. 1 is a top perspective view of a liquid baffle assembly constructed in accordance with the present invention and mounted between a pipetter and a pipette tip.

FIG. 2 is an enlarged top plan view of the baffle assembly of FIG. 1.

FIG. 3 is a fragmentary side elevation view, in cross-section, of the baffle assembly of FIG. 1 taken substantially along the plane of line 3—3 of FIG. 2.

BEST MODE OF CARRYING OUT THE INVENTION

Figure 6:
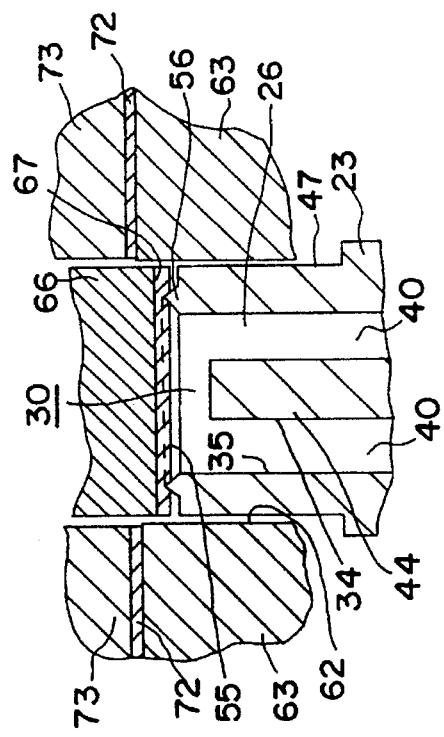
FIG. 6 is a fragmentary, enlarged, side elevation view, in cross-section, of a nose portion of the baffle assembly of FIG. 5, and illustrating sealing of the filter membrane to the baffle assembly.

Reference will now be made in detail to the preferred embodiments of the invention. While the present invention has been described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims.

It will be noted here that for a better understanding, like components are designated by like reference numerals throughout the various figures. Briefly, attention is directed to FIG. 1 where a typical mechanically adjustable pipetter assembly 10 is illustrated which includes a pipette tip mounting end 11. Pipetter 10 typically includes a piston and cylinder arrangement (not shown) which is generally of a known diameter and is coupled to a calibration mechanism 12 disposed proximate the upper end of pipetter assembly 10. Calibration mechanism 12 permits the research technician to variably adjust the stroke of the piston; and hence, adjust the volume of air displaced by the piston. The calibration mechanism 12 generally includes a button 13 and an adjustable knob 14 mounted on the side of pipetter assembly 10 which permits the user to adjust the pipetting volume. Volume indicator indicia 15 positioned on button 13 indicate the proposed volume of fluid to be reasonably accurately drawn or dispensed. Typical of such fixed and adjustable pipetters are those sold under the trademarks EPPENDORF®, PIPETMAN™, FINNPIPETTE, EXCALIBUR®, SOCOREX and OXFORD®, to name a few.

Once set, button 13 may be depressed to displace the desired volume of air from the cylinder. Upon the return stroke of the piston, a corresponding volume of fluid is drawn into a reservoir of pipette tip 16. Briefly, pipette tips 16 are usually disposable and are slidably and frictionally secured to the barrel or tip mounting end 11 located at the bottom distal end of pipetter assembly 10. Pipette tips 16 are usually hollow conical members providing a fluid receiving chamber 17 therein which tapers inwardly from a pipetter securing end 20 of the tip towards a liquid contacting end 21. These pipette tips most typically are injection molded from a plastic, such as polypropylene, although they can also be formed from other materials including glass.

When pipetter assembly 10 creates a sufficient suction, sample fluid 22 is drawn and stored in receiving chamber 17 of pipette tip 16. It is generally during this phase of pipetting that liquid aspiration can occur and pipetter barrel end 11 or the piston of the pipetter assembly can be contaminated through aerosol or fluid transport to the pipetter.

To overcome this problem and in accordance with the present invention, a liquid baffle assembly or adapter, generally designated 23, is positioned between the pipette tip mounting end 11 of the pipetter assembly 10 and securing end 20 of pipette tip 16. Baffle assemble 23 substantially reduces the possibility of transfer of liquid to the pipetter end 11.

Baffle assembly 23 includes a barrier structure 25 (FIG. 3) which is positioned transversely across the upper end of pipette tip receiving chamber 17 and provides at least one narrow circular passageway, generally designated 26, extending in the direction of a longitudinal axis 27 through baffle assembly 23 between an entrance 30 and an exit 31 of passageway 26. The barrier structure passageway includes a first interior wall 32 oriented transverse to, and preferably generally perpendicular to, longitudinal axis 27 to define at least one elbow portion positioned between passageway entrance 30 and exit 31.

Accordingly, the present invention substantially reduces contamination of the pipetter barrel and the pipetter piston, caused by both aerosol transport and/or direct liquid flow through rapid overdraws or splashing or the like. Moreover, by positioning baffle assembly 23 between the pipette tip and the pipetter assembly, not only is the accuracy and precision of the pipetter maintained, but the effective storage and dispensing capacity of chamber 17 pipette tip 16 is not compromised.

Baffle assembly 23 is preferably formed as by an injection molded, disposable adapter (of a thermoplastic material similar to the disposable pipette tips) removably mounted between both the reservoir tip and the pipetter assembly (FIG. 3) so that aspiration of any liquid caused by the pipetter must flow through the adapter. Hence, before each new fluid sample is pipetted, the technician could simply replace and discard both pipette tip 16 and adapter assembly 23. It will be appreciated, however, that baffle assembly 23 could be integrally formed with either pipetter assembly 10 or the pipette tip 16 without departing from the true spirit and nature of the present invention.

In accordance with the present invention, the passageway 26 is formed between inner wall 34 and outer wall 35 of barrier structure 25, which passageway is of a length (L) substantially greater than the spacing therebetween (i.e., width (W) (FIG. 3)). It will be understood that the length to width ratio (L:W) should be at least about 10:1, and is preferably about 15:1. This ratio assures that the aerosol must pass through a long relatively narrow passage through the barrier structure, which increases the possibility of the aerosol particles contacting the baffle walls. Further, passageway 26, proximate exit 31, includes at least one elbow portion 33 along the pathway, and is formed by an interior wall 32 which is positioned substantially perpendicular to longitudinal axis 27 of the barrier structure 25. Thus, this combination of the 90° turn of interior wall 32 together with the length to width ratio of the passageway of at least about 10:1 substantially reduces or inhibits transfer of the aerosol and/or drawn liquid into pipetter barrel 11. Due to the probable frictional contact of the aerosol or sample liquid with either opposing wall 34, 35 or with transverse wall 32, the kinetic energy of the aerosol particles in the passageway is dissipated, causing fluids to condense on the baffle walls. The condensed sample fluid is redirected back into liquid receiving chamber 17 thereby avoiding contact with the pipetter barrel, and hence contamination.

Moreover, to further inhibit the aerosol and/or liquid travel through passageway 26, a second interior wall 36 is provided extending generally parallel to longitudinal axis 27. Baffle wall 36, therefore, forms a second elbow portion in baffle structure 25. By positioning second elbow portion 37 sequentially downstream from the first elbow portion, the flow pathway must pass through two consecutive 90° turns further assuring that the aerosol and fluids are not transported to the pipetter barrel.

In the preferred embodiment, passageway 26 is provided partially by a narrow annular recess portion 40 (FIGS. 3 and 4) extending longitudinally along barrier structure 25 from passageway entrance 30 to a position proximate exit 31. Annular recess 40 is formed between circular inner wall 34 and opposing circular outer wall 35, and, as previously indicated, is of a length (L) at least ten (10) times that of the spacing (W) between the opposing walls 34, 35. Moreover, annular recess 40 provides passageway 26 which is large enough to assure a proper draw of the pipetter. Too restrictive of a passageway may create a substantial venturi effect which can cause any aerosol to jettison into the pipetter barrel, regardless of the frictional contact with opposing walls 34, 35 and elbow walls 32 and 36. Annular recess 40 also preferably tapers inwardly as the passageway extends from entrance 30 towards the exit. This slight taper helps induce contact with opposing walls 34, 35 as well as simplify molding.

FIGS. 2 and 3 further illustrate that annular recess 40 of passageway 26 terminates at four independent channels 41 extending through the barrier structure to exit end 31. These small channels 41 are preferably circumferentially spaced about axis 27 and provide a means of communication between the exit and the entrance of the passageway upon which the permits proper operation of the pipetter assembly.

As best illustrated in FIGS. 2 and 3, channels 41 are formed between a cross-shaped support rib 42 positioned in the path of passageway 26 at exit 31. Support ribs 42 in combination with passage exit 31 form funnel portions 43 which together prevent the flow of fluid into the pipetter. Moreover, channels 41 formed therebetween have transverse cross-sectional areas which are substantially reduced for further restriction.

At an opposite end of baffle assembly 23 is a post portion 44 which is suspended downward therefrom providing the inner wall 34 necessary to form annular recess 40 with outer wall 35. While support rib 42 is preferably integrally molded with barrier structure 25, it will be understood that support rib 42 and post portion 44 could be formed as an insert press fit into passageway 26 without departing from the true spirit and nature of the present invention.

As above-indicated, baffle assembly 23 is preferably formed as an adapter removably mounted between the pipetter assembly and the pipette tip. One end of barrier structure 25 of baffle assembly 23 provides a tapered receiving bore 45 formed and dimensioned for removable receipt of tip mounting end 11 of pipetter assembly 10. FIG. 3 shows that a barrel outer surface 46 of the tip mounting end 11 frictionally engages receiving bore 45 for removable retainment therewith. Similarly, an opposite nose portion end 47 of baffle assembly 23 is formed and dimensioned for removable insertion into a securing end bore 50 of pipette tip 16. The outer peripheral surface of nose portion 47 frictionally engages securing end bore 50 for removable retainment therewith. Upon further insertion into securing end bore 50, an upper ledge 52 of tip 16 seats against shoulders 53 of vertically extending rib portions 54 of the baffle assembly.

In the preferred embodiment of the present invention, an aerosol filter membrane, generally designated 55, is provided mounted to barrier structure 25 of baffle assembly 23 along passageway 26 in a manner reducing transfer of aerosol from receiving chamber 17 to pipetter assembly 10. Such an additional filter membrane 55 is necessary for extremely aerosol sensitive operations, such as PCR. Accordingly, filter membrane 55 and passageway 26 of the baffle assembly cooperate to substantially reduce any possibility of aerosol and/or sample fluid from reaching and contacting the pipetter barrel.

Filter membrane 55 is preferably provided by a 0.45 micron nitrocellulose transfer membrane which is capable of filtering out all or substantially all aerosol. In accordance with the present invention, membrane 55 is to be heat fused to the distal end of nose portion 47 (FIGS. 3 and 6) of the baffle assembly about the perimeter of passageway entrance 30. To promote heat fusion at the nose portion of the baffle assembly, an annular energy director ring 56 preferably protrudes outwardly from the distal end of nose 47, which causes or induces localized heating at an annular apex edge 60 thereof for fusion of filter membrane 72 to nose 47.

Figure 5:
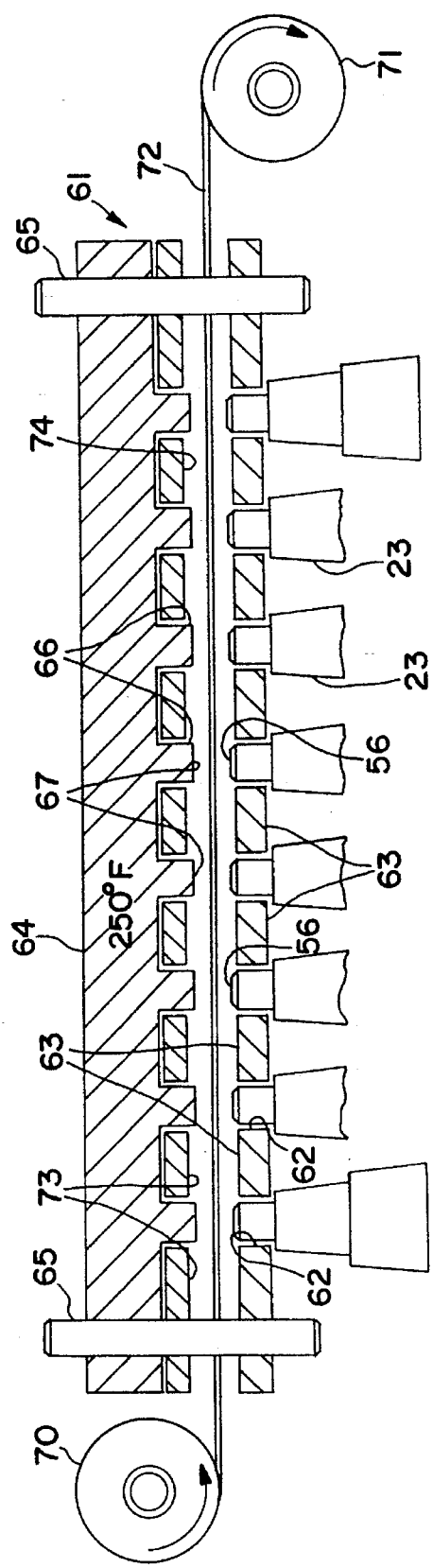
FIG. 5 is a side elevation view, in cross section of sheet of filter membrane material being simultaneously heat sealed to independent ends of an array of baffle assemblies of FIG. 2 in accordance with the present invention.

In the preferred form, the filter mounting process is simultaneously performed on an 8×12 array (i.e., 96) of adapter or baffle assemblies positioned in a heat fusing assembly 61 shown in FIG. 5. While 96 is typically the industry standard of manufacture for related medical research devices, the filter mounting process may be performed on as little as two (2) assemblies.

Briefly, each baffle 23 in the array is oriented in manner placing nose portion 47 upwardly and protruding through apertures 62 of a shearing plate 63. A heating plate 64 is positioned opposite shearing plate 63, and is movably mounted to guide pins 65 for reciprocating movement toward and away from the array of adapter assemblies. The heating plate 64 includes a plurality of heating posts 66 extending downwardly therefrom in aligned and opposed relationship to the array of baffle nose portions. Each heating post 66 includes a substantially planar heating surface 67 aligned with a corresponding nose portion distal end of adapter or baffle assembly 23.

Figure 4:
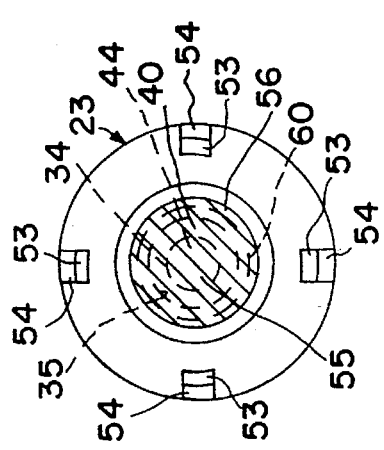
FIG. 4 is a bottom plan view of the baffle adapter assembly of FIG. 2.

FIGS. 5 and 6 illustrate that fusing assembly 61 includes a filter membrane paper roll 70 on one end thereof, and a filter paper waste roll 71 on an opposite end thereof with a sheet 72 of membrane paper therebetween. Upon alignment of a fresh sheet 72 of paper membrane between the heating plate and the array of adapters, heating plate 64 is moved along guide pins 65 toward the baffles 23 until the corresponding heating surfaces 67 sandwich the filter membrane against the nose portion distal ends (FIG. 6). Each heating post 66 applies a pressing force against the annular apex edge 60 of the energy director ring 56 of about 1–5 lbs. at a temperature of about 250° F. for about 0.5–5 seconds. As apex edge 60 of the energy director ring 56 locally melts due to contact with the corresponding heating surface, it flows into the pores of the filter paper, causing fusion therebetween. Accordingly, energy director ring 56 causes localized heating to partially melt through and fuse with the membrane paper about the perimeter of the passageway entrance (FIGS. 4 and 6).

Subsequently, as the heating plate 64 is moved away from the adapter assemblies, shearing plate 63 simultaneously moves along guide pins 65 therewith until apertures 62 move above the nose portion distal ends by a distance sufficient to shear the filter membrane paper therefrom. A stripper plate 73, opposing shearing plate 63, is further provided which is moved back toward the array of adapter or baffle assemblies 23 to strip portions of the membrane paper still stuck to the heating posts 66. The used cellulose transfer paper is then rolled onto the filter paper waste roll 71.

It will be appreciated that sheet 72 may be positioned and aligned between the heating plate and the array of adapters in the most efficient arrangement possible to make efficient use of the filter material. It will be further be understood that post portion 44 does not extend all the way to the distal end of securing end 20 of baffle assembly 23 to contact filter membrane 24. This creates a larger cross-sectional area of the passageway entrance 30 which reduces the pressure applied to the filter membrane during aspiration. Hence, unlike the prior art aerosol filter tips, the resistance across the filter membrane can be distributed which reduces resistance. In turn, the pipetter assembly may be operated with the intended precision and accuracy.

In another aspect of the present invention, a method of mounting an aerosol resistant filter membrane 24 to a heat deformable nose portion 47 of a pipetter assembly 10 is provided. The method comprising the steps of: positioning the filter membrane 24 onto a distal end of nose portion 47 and over passageway entrance 30; and heating a perimeter of nose portion 47 about entrance 30 to a temperature sufficient to cause heat fusion between filter membrane 24 and nose portion 47.

The heating step is accomplished by pressing a heating plate 64 against a backside of filter membrane 24 to sandwich the filter membrane between apex edge 60 and heating surface 67. As mentioned, an array of adapter assemblies 23 is provided aligned in rows and columns. The positioning step is accomplished by placing a sheet of filter membrane material 72 over the array of nose portion distal ends in abutting contact therewith for simultaneous heat fusion thereto. Hence, in the preferred form, 96 adapter tips are covered and sealed in one touch of the heating element.

What is claimed is:

1. A liquid baffle adapter assembly positioned between a pipetter assembly formed for drawing and dispensing a liquid, and a pipette tip device including a liquid drawing end and an opposite pipetter securing end formed for removably securement to a pipette tip mounting end of said pipetter assembly, said pipette tip device defining a liquid receiving chamber extending from said liquid drawing end to said pipetter securing end along a longitudinal axis thereof, said baffle adapter assembly comprising:

a barrier structure molded together with said adapter assembly as a unit, and defining a receiving bore formed and dimensioned for snug removable receipt of said tip mounting end of said pipetter assembly, and an opposite nose portion formed and dimensioned for snug removable engagement with said pipetter securing end of said pipette tip device, said barrier structure extending transversely across said pipette tip liquid receiving chamber and defining an elongated passageway extending in the direction of said longitudinal axis through said barrier structure between an entrance at said nose portion and an exit at said receiving bore, said passageway being defined by substantially vertical walls tapering inwardly from said entrance toward said exit, and having substantial surface area relative a transverse cross-sectional area of said passageway for condensing aerosol thereon upon contact with said vertical walls, said passageway further being narrow relative the passageway longitudinal length, and including a first wall portion extending substantially perpendicular from one of said vertical walls and extending substantially across said passageway, and a plurality of oppositely facing second wall portions axially spaced in a direction toward said entrance from said first wall portion and extending substantially perpendicularly from the other one of said vertical walls in a direction away from said passageway to define with said first wall portion a plurality of spaced apart elbow-shaped channels positioned in said passageway between said entrance and said exit.

2. The adapter assembly as defined in claim 1 wherein, said nose portion tapers inwardly toward one distal end thereof, and
said receiving bore tapers outwardly toward an opposite distal end thereof.

3. The adapter assembly as defined in claim 1 wherein, said passageway is of a length substantially greater than a width thereof.

4. The adapter assembly as defined in claim 3 wherein, a ratio of said passageway length to said passageway width is at least about 10:1.

5. The adapter assembly as defined in claim 3 wherein, said vertical walls include an inner facing wall and an outer facing wall forming an annular-shaped passageway extending longitudinally through said barrier structure from said entrance and terminating proximate said exit.

6. The adapter assembly as defined in claim 1 wherein, said elbow shaped channels each extends radially inwardly toward said longitudinal axis.

7. The adapter assembly as defined in claim 1 wherein, said passageway includes at least two third wall portions extending generally parallel to said longitudinal axis from said second wall portions to define second elbow-shaped channels positioned sequentially with respect to the first named elbow-shaped channels between said entrance and said exit.

8. The adapter assembly as defined in claim 1 wherein, said elbow-shaped channels are positioned proximate said receiving bore.

9. The adapter assembly as defined in claim 1 wherein, said passageway exit terminates into a funnel portion defined by said barrier structure and extending into a bottom portion of said receiving bore, said funnel portion further tapering outwardly toward said pipetter mounting tip end.

10. The adapter assembly as defined in claim 1 wherein, said passageway includes at least four independent, elbow-shaped channels, in parallel, positioned circumferentially about and extending in the direction of said longitudinal axis, each said channel being substantially narrower than said passageway, and each including said first wall portion extending generally perpendicular to said longitudinal axis to define the respective elbow-shaped channels positioned between said passageway entrance and said exit.

11. The adapter assembly as defined in claim 10 wherein,
said vertical walls include an inner facing wall and an outer facing wall forming an annular-shaped passageway communicating and intersecting each channel, and extending longitudinally along said barrier structure from said entrance and terminating proximate said exit.

12. The adapter assembly as defined in claim 10 wherein,
each said channel includes at least two third wall portions extending generally parallel to said longitudinal axis to define respective second elbow-shaped channels positioned sequentially with the respective first named elbow-shaped channels between said entrance and said exit.

13. The adapter assembly as defined in claim 1 further including:
an aerosol filter member coupled to said barrier structure and along said passageway in a manner substantially reducing transfer of aerosol from said receiving chamber to said pipette tip mounting end of the pipetter assembly.

14. The adapter assembly as defined in claim 13 wherein,
said aerosol filter member is disposed on the distal end of said nose portion.

15. The adapter assembly as defined in claim 14 wherein,
said distal end of said nose portion defines a fusing edge outwardly protruding therefrom and positioned proximate said passageway entrance, said fusing edge being adapted to fuse said aerosol filter member about a perimeter of the nose portion distal end.

16. The adapter assembly as defined in claim 15 wherein,
said fusing edge is heat deformable to fuse said filter member thereon, and extends continuously around said perimeter thereof.

* * * * *